US012083256B2

(12) United States Patent
Moreau et al.

(10) Patent No.: US 12,083,256 B2
(45) Date of Patent: Sep. 10, 2024

(54) INTEGRATION OF UV LIGHT INTO AIRCRAFT AIR MANAGEMENT SYSTEMS

(71) Applicant: Hamilton Sundstrand Corporation, Charlotte, NC (US)

(72) Inventors: Claude J. Moreau, Vernon, CT (US); Blair A. Smith, South Windsor, CT (US); Vijay V. Pujar, Rancho Santa Fe, CA (US); Steven Poteet, Ashland, MA (US); Lance R. Bartosz, Granby, MA (US)

(73) Assignee: HAMILTON SUNDSTRAND CORPORATION, Charlotte, NC (US)

( * ) Notice: Subject to any disclaimer, the term of this patent is extended or adjusted under 35 U.S.C. 154(b) by 647 days.

(21) Appl. No.: 17/244,221

(22) Filed: Apr. 29, 2021

(65) Prior Publication Data
US 2021/0338877 A1    Nov. 4, 2021

Related U.S. Application Data

(60) Provisional application No. 63/028,175, filed on May 21, 2020, provisional application No. 63/018,222, filed on Apr. 30, 2020.

(51) Int. Cl.
*A61L 9/20* (2006.01)
*B64D 13/06* (2006.01)

(52) U.S. Cl.
CPC ............. *A61L 9/20* (2013.01); *B64D 13/06* (2013.01); *A61L 2209/14* (2013.01); *A61L 2209/16* (2013.01); *B64D 2013/0651* (2013.01); *B64D 2013/0688* (2013.01)

(58) Field of Classification Search
CPC ............. A61L 9/20; A61L 2209/16; B64D 2013/0688
See application file for complete search history.

(56) References Cited

U.S. PATENT DOCUMENTS

| | | |
|---|---|---|
| 7,300,499 B1 | 11/2007 | Fleisher |
| 7,789,346 B2 | 9/2010 | Horstman et al. |
| 10,322,811 B2 | 6/2019 | Breigenzer et al. |
| 2003/0177777 A1 | 9/2003 | Brumett |
| 2007/0053188 A1 | 3/2007 | New et al. |

(Continued)

FOREIGN PATENT DOCUMENTS

WO    2006131049 A1    12/2006

OTHER PUBLICATIONS

Extended European Search Report; European Application No. 2117061. 7-1010; Date: Sep. 2, 2021; 14 Pages.

(Continued)

*Primary Examiner* — Sean E Conley
*Assistant Examiner* — Justin Hwang
(74) *Attorney, Agent, or Firm* — CANTOR COLBURN LLP

(57) ABSTRACT

An air management system of a vehicle having a conditioned area includes at least one duct defining a flow path for delivering air to the conditioned area and a sterilization system associated with the at least one duct. The sterilization system including at least one light source operable to emit a germicidal ultraviolet light into the flow path defined by the at least one duct to sterilize the air to be provided to the conditioned area.

20 Claims, 5 Drawing Sheets

(56) References Cited

U.S. PATENT DOCUMENTS

| | | | |
|---|---|---|---|
| 2008/0213129 A1* | 9/2008 | van der Pol | F24F 8/22 |
| | | | 422/24 |
| 2011/0171090 A1 | 7/2011 | Johnson et al. | |
| 2012/0273340 A1 | 11/2012 | Felix | |
| 2015/0064061 A1 | 3/2015 | Taghipour | |
| 2015/0064069 A1* | 3/2015 | Yi | A61L 9/20 |
| | | | 422/121 |
| 2015/0202107 A1* | 7/2015 | Khan | B01D 47/021 |
| | | | 96/361 |
| 2017/0197493 A1* | 7/2017 | Paranhos | A61L 2/10 |
| 2019/0009912 A1* | 1/2019 | Matsui | B64D 13/02 |
| 2019/0100318 A1 | 4/2019 | Space et al. | |
| 2020/0108166 A1 | 4/2020 | Rhoden | |
| 2020/0122078 A1 | 4/2020 | Trent et al. | |

OTHER PUBLICATIONS

European Office Action; European Application No. 21170761.7; dated Mar. 13, 2023; 19 pages.

\* cited by examiner

INTEGRATION OF UV LIGHT INTO AIRCRAFT AIR MANAGEMENT SYSTEMS

CROSS-REFERENCE TO RELATED APPLICATIONS

This application claims the benefit of U.S. Provisional Application No. 63/018,222 filed Apr. 30, 2020, and U.S. Provisional Application No. 63/028,175 filed May 21, 2020, the disclosures of which are incorporated herein by reference in their entirety.

BACKGROUND

Embodiments of the disclosure relate to an air management system used to provide air to one or more compartments intents within a vehicle, and more specifically, to a system for sterilizing a portion of the air management system and the air therein.

Pressurized aircraft have integrated air management systems to provide a pressurized environment, fresh air transfer, recycling, heating, and air conditioning to maintain a comfortable safe environment for occupants for extended periods. Air recycling and replacing stale air requires continuous scrubbing for cleanliness to minimize airborne dust, dirt, odors, viruses, spores, and bacteria. This cleaning or scrubbing of the air is typically performed via physical, electrostatic or chemical filtration, such as via a HEPA filter. However, bacteria and dirt can accumulate on the filter, requiring cleaning or replacement of the filters themselves.

BRIEF DESCRIPTION

According to an embodiment, an air management system of a vehicle having a conditioned area includes at least one duct defining a flow path for delivering air to the conditioned area and a sterilization system associated with the at least one duct. The sterilization system including at least one light source operable to emit a germicidal ultraviolet light into the flow path defined by the at least one duct to sterilize the air to be provided to the conditioned area.

In addition to one or more of the features described above, or as an alternative, in further embodiments the germicidal ultraviolet light has a wavelength between about 200 nm and about 280 nm.

In addition to one or more of the features described above, or as an alternative, in further embodiments air within the at least one duct has a first flow rate at a first portion of the at least one duct and a second flow rate at a second portion of the at least one duct, the second flow rate being slower than the first flow rate, the at least one light source being positioned to emit the germicidal ultraviolet light within the second portion of the at least one duct.

In addition to one or more of the features described above, or as an alternative, in further embodiments comprising a filter mounted within the second portion of the at least one duct, the at least one light source being positioned to emit the germicidal ultraviolet light over a portion of the filter.

In addition to one or more of the features described above, or as an alternative, in further embodiments comprising a filter mounted within the at least one duct, wherein the at least one light source is positioned to emit germicidal ultraviolet light over a portion of the filter.

In addition to one or more of the features described above, or as an alternative, in further embodiments a surface of the at least one duct associated with the at least one light source is reflective.

In addition to one or more of the features described above, or as an alternative, in further embodiments the at least one light source at least one light source operable to emit a germicidal ultraviolet light into the flow path defined by the at least one duct includes a first light source and a second light source, spaced from the first light source, wherein the germicidal ultraviolet light emitted by the first light source overlaps with the germicidal ultraviolet light emitted by the second light source.

In addition to one or more of the features described above, or as an alternative, in further embodiments the first light source and the second light source are mounted in vertical alignment.

In addition to one or more of the features described above, or as an alternative, in further embodiments the first light source and the second light source are mounted adjacent opposite sides of the at least one duct.

In addition to one or more of the features described above, or as an alternative, in further embodiments the first light source and the second light source are mounted at adjacent sides of the at least one duct.

In addition to one or more of the features described above, or as an alternative, in further embodiments comprising: an air source, an environmental control system in fluid communication with the air source, a cabin air recirculation system fluidly connected to an outlet of the conditioned area, an air mixing unit connected to the environmental control system and to the cabin recirculation air system, and an air distribution system extending from the air mixing unit to one or more vents associated with the conditioned area.

In addition to one or more of the features described above, or as an alternative, in further embodiments the at least one duct is a part of the cabin recirculation air system.

In addition to one or more of the features described above, or as an alternative, in further embodiments the at least one duct is the air mixing unit.

In addition to one or more of the features described above, or as an alternative, in further embodiments the at least one duct is a part of the air distribution system.

In addition to one or more of the features described above, or as an alternative, in further embodiments the conditioned area is a cabin of an aircraft.

In addition to one or more of the features described above, or as an alternative, in further embodiments the air is cabin recirculation air provided from an outlet of the conditioned area.

In addition to one or more of the features described above, or as an alternative, in further embodiments the sterilization system is operational when the aircraft is in flight.

In addition to one or more of the features described above, or as an alternative, in further embodiments the at least one light source includes a plurality of light sources, wherein the plurality of light sources and an intensity of each of the plurality of light sources is determined based on at least one of a volume flow rate and a humidity of the air.

In addition to one or more of the features described above, or as an alternative, in further embodiments the air is dehumidified upstream from the sterilization system.

In addition to one or more of the features described above, or as an alternative, in further embodiments the air is rehumidified downstream of the sterilization system.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figures.

Figure 1:
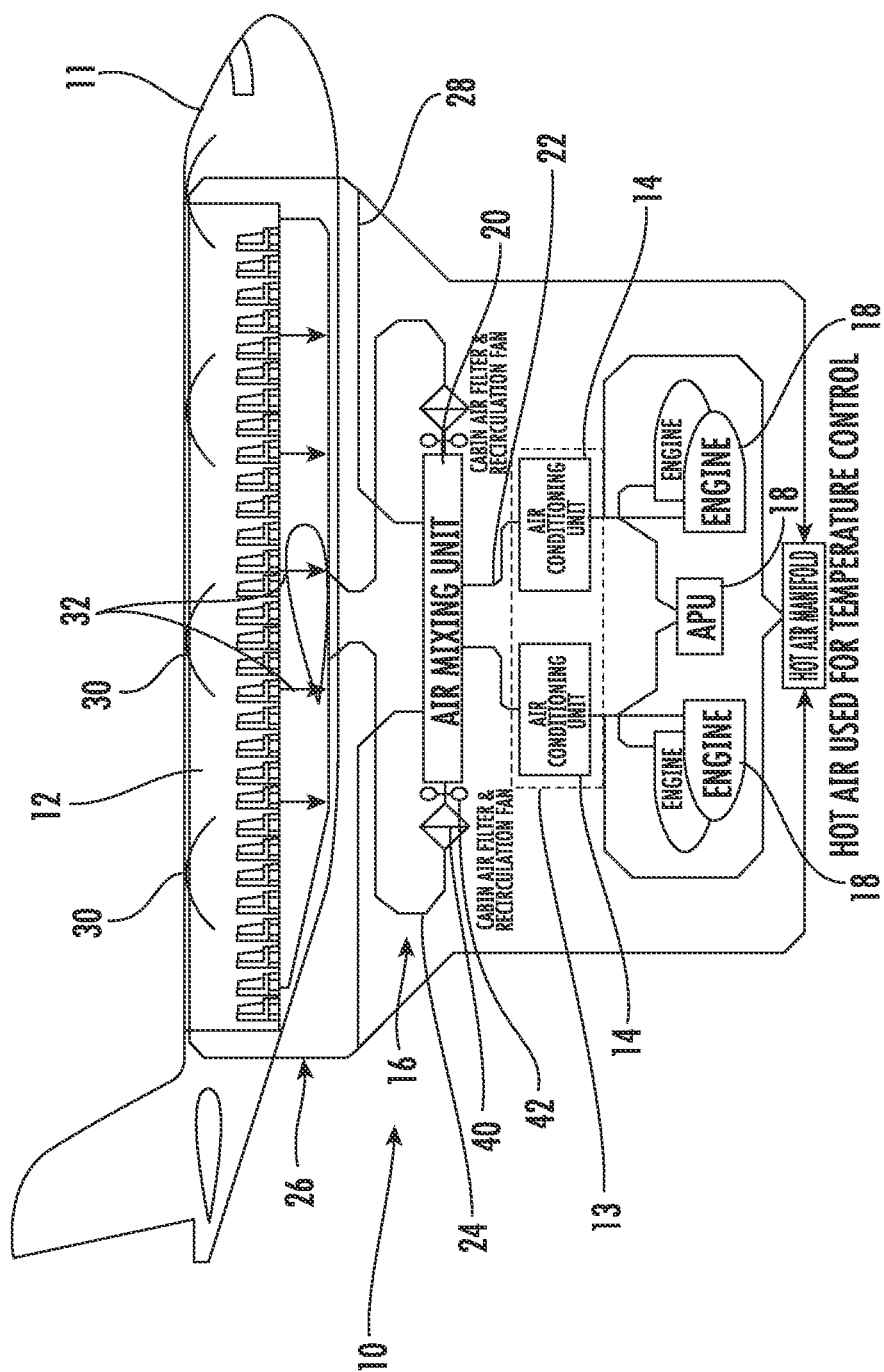
FIG. 1 is a schematic diagram of an air management system of an aircraft.

With reference now to FIG. 1, a schematic of an example of an air management system 10 to control the air of a vehicle, such as an aircraft 11 is illustrated. The aircraft 11 includes a pressurized area or cabin 12 that the air management system 10 controls. The cabin 12 may be configured to house people, cargo, and the like therein. The air management system 10 provides conditioned air to, and removes used or contaminated air from, the cabin 12. The air management system 10 includes an environmental control system 13 having at least one air conditioning unit or pack 14, and a cabin air recirculation sub-system 16. While the air management system 10 is illustrated and described herein with reference to an aircraft 11, it should be understood that the systems and techniques discussed herein may be used for a variety of air management systems 10. For example, the cabin 12 may be replaced with any closed volume to be conditioned. As such, systems described herein may be used with ship air management systems, such as submarines and cruise liners for example, personnel carrier air management systems, bus, trolley, train, or subway air management systems, or any other air management system that requires a continual supply of conditioned air.

As shown in the FIG. 1, a medium, such as air for example, is provided from one or more sources 18 to the air management system 10. Examples of suitable sources 18 include but are not limited to an engine of the aircraft 11 and an auxiliary power unit of the aircraft 11. The medium output from these sources 18 is provided to the one or more air conditioning units 14 of the environmental control system 13. Within these air conditioning units 14, the medium is conditioned. This conditioning includes altering one or more of a pressure, temperature, humidity, or flow rate of the medium based on an operating condition of the aircraft. The medium output or discharged from the one or more air conditioning units 14 of the environmental control system 13 may be used maintain a target range of pressures, temperatures, and/or humidity within the cabin 12.

The medium discharged from the air conditioning units 14 is provided to an air mixing unit or mixing manifold 20 via one or more outlet ducts 22. Similarly, at least one duct 24 of the cabin air recirculation sub-system 16 extends from the cabin 12 to the air mixing unit 20 to deliver air exhausted from the cabin 12 to the air mixing unit 20. Within the air mixing unit 20, the cabin recirculating air is mixed with the medium output from the one or more air conditioning units 14 to achieve a mixed medium having one or more desired parameters, such as temperature, pressure, and humidity for example.

In an embodiment, the mixed medium is delivered to the cabin 12 from the air mixing unit 20 via an air distribution system 26 including one or more conduits 28. As shown, the mixed medium may be delivered to the cabin 12 and cockpit via a ventilation system arranged near a ceiling of the cabin 12. In some embodiments, the mixed medium typically circulates from the top of the cabin 12 toward the floor and is distributed to a plurality of individual vents 30 of the ventilation system spaced laterally between the front and rear of the cabin 12. It should be understood that the air management system 10 illustrated and described herein is intended as an example only, and that any suitable air management system is within the scope of the disclosure.

Figure 2:
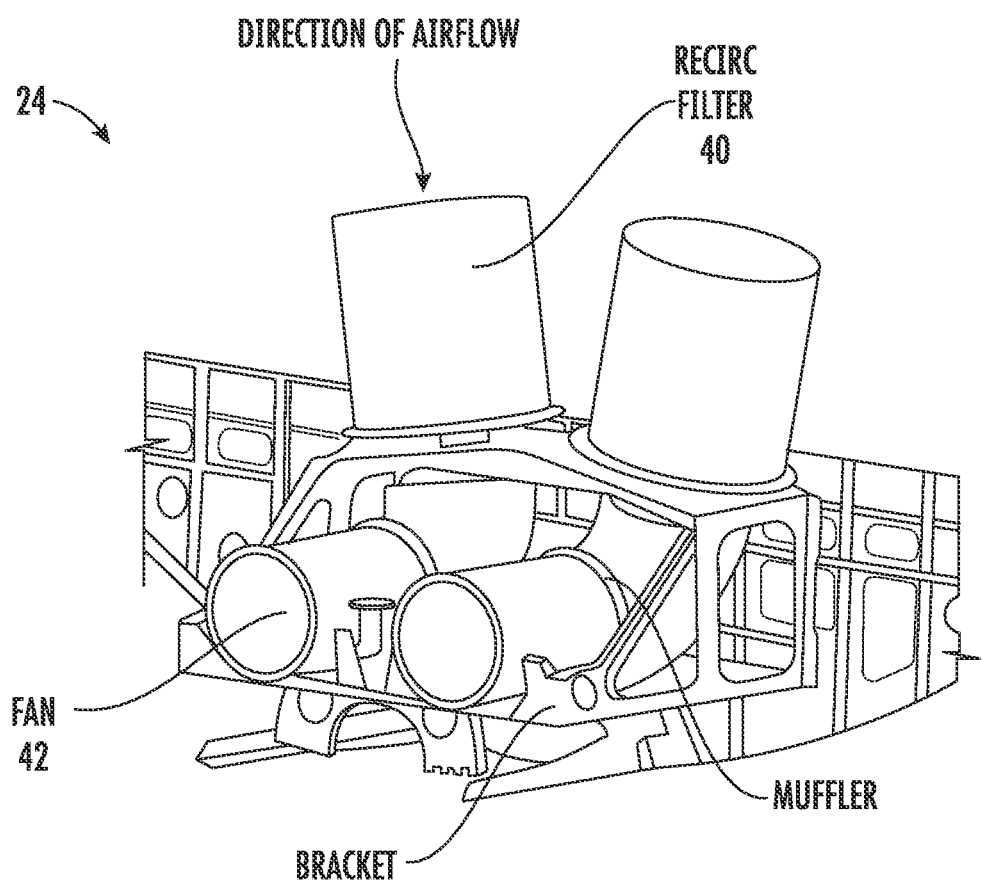
FIG. 2 is a perspective view of a portion of the cabin air recirculation sub-system within an aircraft air management system according to an embodiment.

With reference now to FIG. 2, an example of a portion of the cabin air recirculation sub-system within the air management system 10 is shown in more detail. In the illustrated, non-limiting embodiment, a portion of the duct 24 of the cabin air recirculation sub-system 16 and fluidly connects one or more outlets 32 (see FIG. 1) of the cabin 12 to the air mixing unit 20. Mounted within the duct is a filter 40 configured to remove bacteria, viruses and particulate matter from the cabin recirculation air provided from the outlets 32 in the cabin 12 as it flows through the filter 40. Although the filter 40 is shown as being arranged adjacent a downstream end of the duct, such as directly upstream from an interface between the duct and the air mixing unit, a filter arranged at any location within the duct is contemplated herein. Further, although the filter 40 is illustrated as having a circular configuration in FIG. 2, and a rectangular configuration in FIG. 3, it should be understood that a filter 40 having any configuration is within the scope of the disclosure. In an embodiment, the filter 40 is a HEPA-type filter. However, any suitable filter, or combination of multiple filters is within the scope of the disclosure. Further, in an embodiment, the duct 24 includes a recirculation fan 42 to establish an overpressure that is used to drive the flow of the recirculating cabin air through the filter 40 and to the air mixing unit 20. However, embodiments of a portion of a cabin air recirculation sub-system 16 that do not include a fan such that air flow through the duct 24 is driven by another source or by pressure for example, are also contemplated herein.

Figure 3:
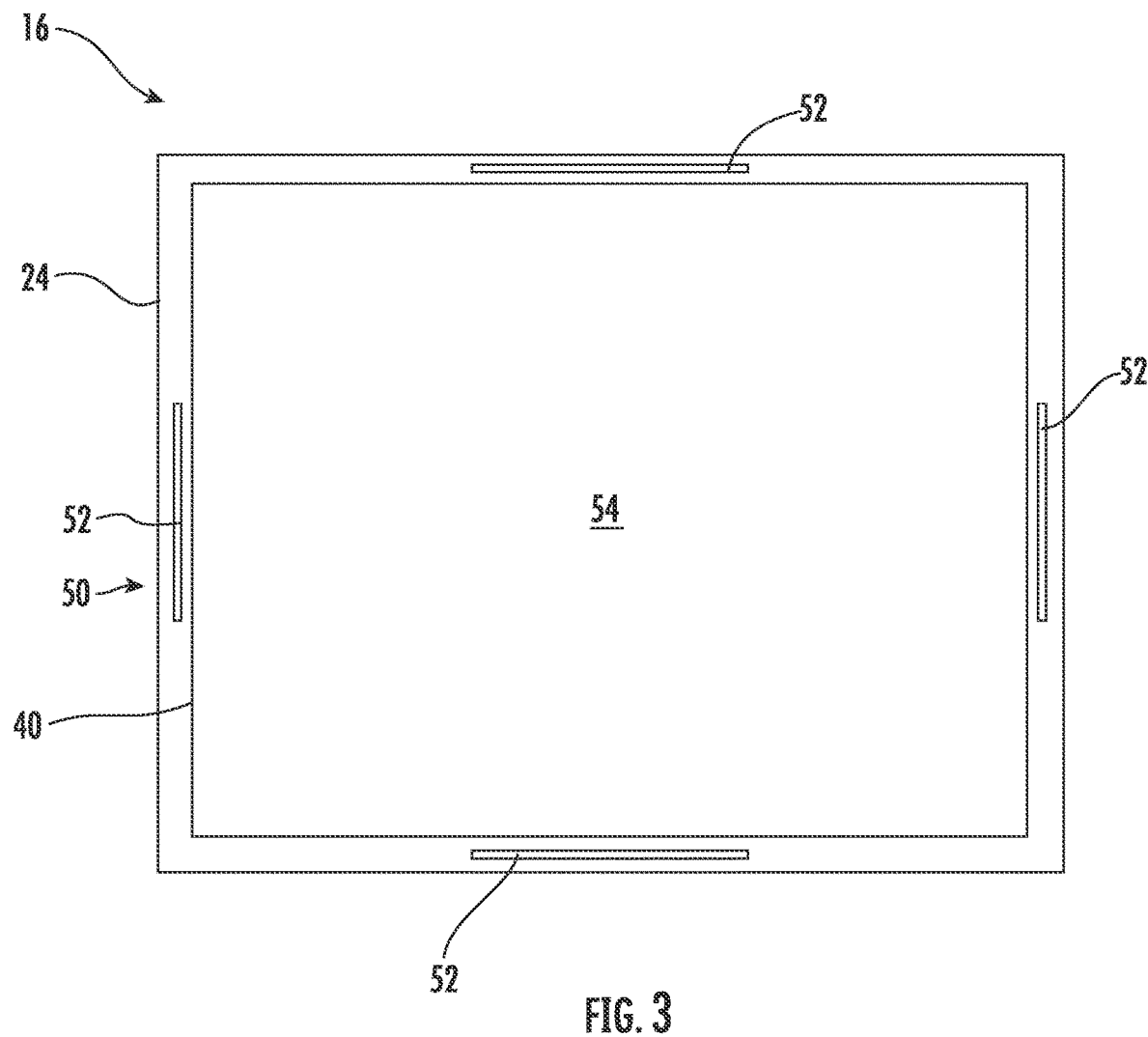
FIG. 3 is a cross-sectional view an air duct including a sterilization system according to an embodiment.
Figure 4:
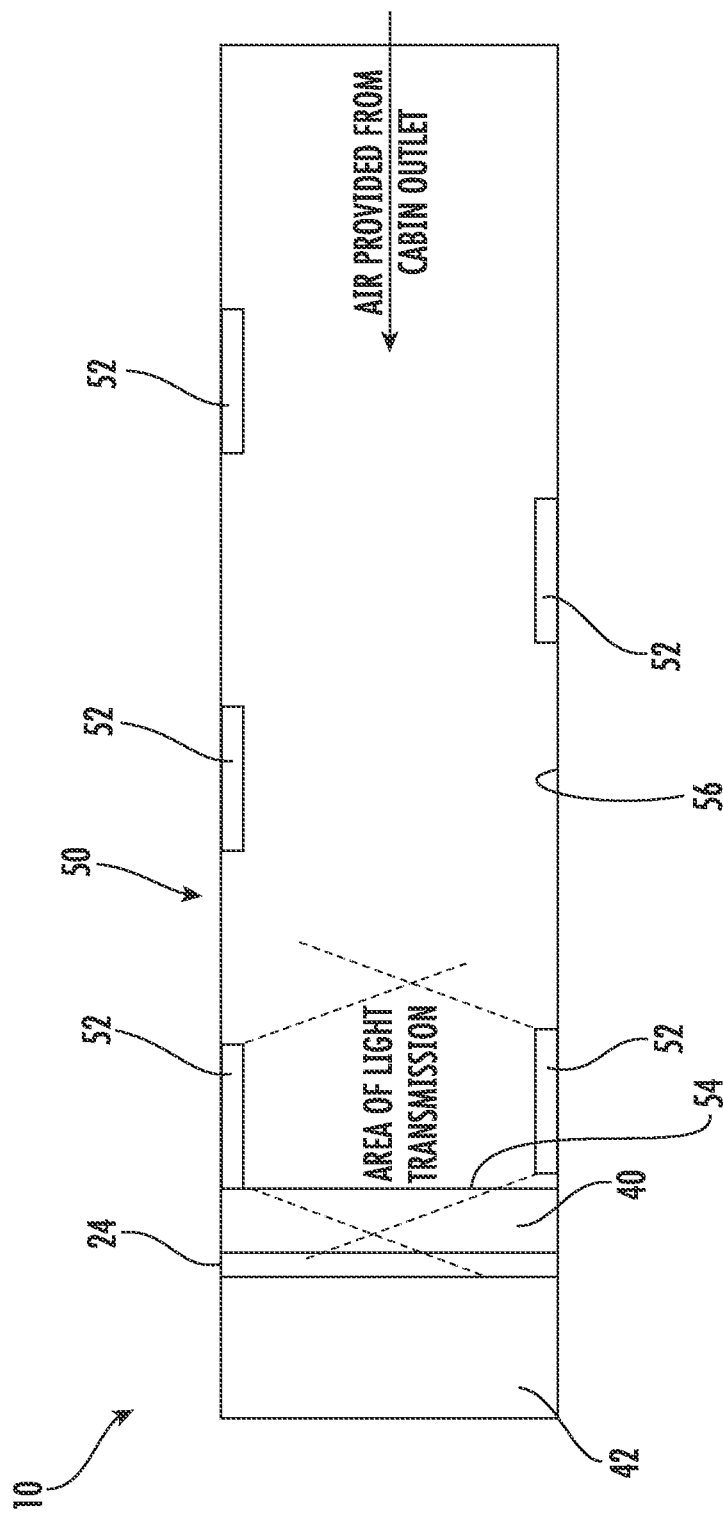
FIG. 4 is a cross-sectional view of a portion of a duct of an air management system including a sterilization system according to an embodiment.
Figure 5:
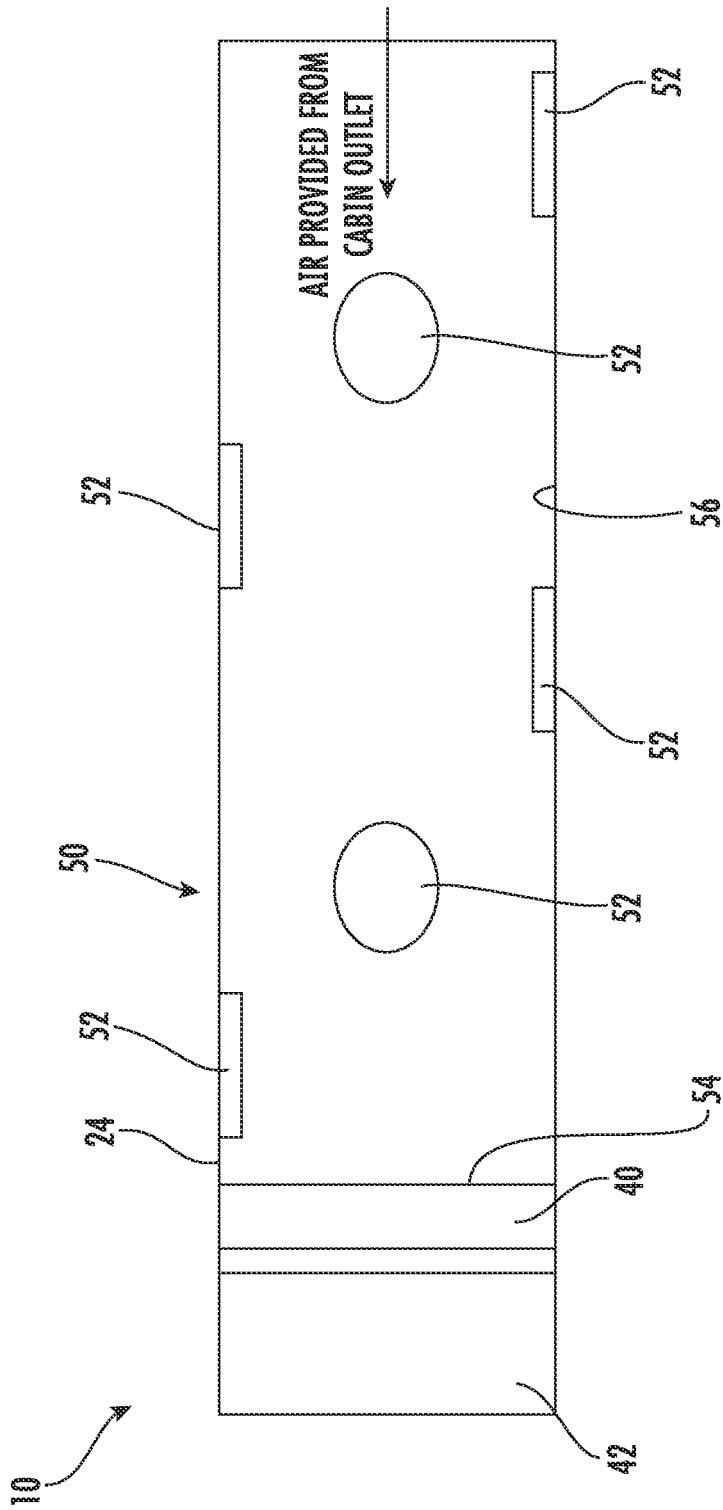
FIG. 5 is a cross-sectional view of a portion of a duct of an air management system including a sterilization system according to an embodiment.

With reference now to FIGS. 3-5, in an embodiment, the air management system 10 additionally includes a sterilization system 50 for sterilizing at least a portion of the air therein. In addition to the removal of particulate matter, the sterilization described herein additionally includes killing or rendering harmless bacteria or airborne viruses within the air management system 10 and/or an air flow there through. Because dehumidified air is easier to sterilize, the air is dehumidified before passing through (upstream from) he sterilization system 50 and is then rehumidified downstream of the sterilization system 50, such as in the air mixing unit 20 for example.

As shown, in an embodiment, the sterilization system 50 is used to sterilize a portion of the air provided to the cabin 12, such as the cabin recirculation air discharged from outlets 32 of the cabin 12 and provided to the air mixing unit 20 and/or a portion of one or more ducts 24 extending between the cabin outlets 32 and the air mixing unit 20. Further, it should be understood that although a duct 24 of the cabin air recirculation system 16 is illustrated and described herein with respect to the sterilization system 50, any portion of the air management system 10, and specifically any portion or duct that is used to move cabin discharge air or cabin recirculation air through the air management system 10, including but not limited to the air mixing unit 20 and the conduits 28 of the air distribution system 26 for example, may be adapted for use with a sterilization system 50 as described herein.

The sterilization system 50 includes at least one light source 52 capable of emitting a light having a wavelength suitable to perform germicidal irradiation. In an embodiment, the light source 52 is operable to emit a germicidal ultraviolet light, such as having a wavelength between about 200 and about 280 nanometers, also known as "UV-C." The wavelength of the light emitted by the light source 52 may further be between about 220 nm and about 260 nm, or about 240 nm and about 260 nm, about 250 nm to about 260 nm, or more specifically 253 nm to 254 nm.

It should be understood that ultraviolet light having another wavelength, such as between 280 nm and 400 nm, and more specifically between 280 nm and 315 nm, or other types of light may also be suitable for use in sterilization applications. Additionally, a light source 52 having any configuration, such as an individual bulb, a light strip having a plurality of bulbs or light emitting diodes, or another type of emitter, is within the scope of the disclosure. In embodiments of the sterilization system 50 including a multiple light sources 52, a configuration of the light sources may be substantially identical, or alternatively, may vary based on a position of the light source 52 relative to the air management system.

The use of germicidal ultraviolet light, and specifically UV-C light, typically requires exposure for only a matter of seconds to kill any virus or bacteria present. However, the length of exposure may vary in response to one or more parameters, such as the wavelength of the light, the intensity or strength of the light, the volume flow rate of air, and the humidity of the air, for example. In an embodiment, the one or more light sources 52 and an intensity of each light source 52 is determined based on at least one of the volume flow rate and the humidity of the air. Because exposure for only a limited period of time is required for sterilization, the one or more light sources 52 may be disposed at one or more areas along the flow path defined by the duct 24.

In an embodiment, the one or more light sources 52 are located at an area of the flow path where the flow of air provided from the cabin outlets 32 is slowest. For example, the flow rate of the cabin recirculation air through the portion of the duct 24 including the filter 40 is reduced relative to the flow rate of the air at an upstream portion of the duct 24 to maximize the efficacy of the filter 40. Accordingly, in an embodiment, one or more light sources 52 are mounted such that the light emitted therefrom projects over at least a portion, and in some embodiments, over substantially the entire surface 54 of the filter 40. As a result, any viruses or bacteria present on the filter 40, such as trapped in the filter material itself, are killed or neutralized. In such embodiments, the one or more light sources 52 may be integrated into the filter 40 (FIG. 3) and/or may be mounted to a portion of the duct 24, such as directly adjacent the filter 40 (FIG. 4), or alternatively, at a location axially offset from the filter 40 (FIG. 5) such that the light emitted from the light sources 52 overlaps the surface the filter 40.

In other embodiments, the sterilization system 50 may alternatively or additionally include one or more light sources 52 arranged at a location where the flow rate of the cabin circulation air is faster than at the filter 40. As shown, one or more light sources 52 may be arranged within the air management system 10 to emit germicidal ultraviolet light over a portion of the flow path defined by the duct 24, upstream from the filter 40, as shown in FIGS. 4 and 5. Although the figures show a sterilization system 50 including a plurality of light sources 52 operable to illuminate substantially the entire length of the duct 24 extending between an upstream end thereof 56 and the filter 40, embodiments where only a portion of the duct 24 is illuminated are also contemplated herein. In some embodiments including multiple light sources 52, each of the plurality of light sources 52 may be positioned such that the light emitted therefrom overlaps with the light emitted from an adjacent light source 52. As shown, the light sources may be mounted within the same plane, such as adjacent the same side of the duct 24, or alternatively, at different sides of the duct 24, such as opposite sides (FIG. 4) or adjacent sides (FIG. 5) for example. As a result, the region of the duct 24 illuminated by the light sources 52 will be free from shadows or non-illuminated areas where bacteria or viruses may accumulate.

Further yet, one or more interior surfaces 56 of the duct 24 within the region illuminated by the one or more light sources 52 may have a reflective or mirrored coating to facilitate increased distribution of the germicidal light throughout the duct 24. A reflective or mirrored coating as described herein may include, but is not limited to, one or more of aluminum, gold, chrome, nickel, titanium, copper, silver, copper oxide, zinc oxide, or another suitable shiny material or polished surface. Further, such a coating may be applied via any suitable method, such as via a spray, dip, wipe, vapor deposition, plating, or other known method. In an embodiment, the coating material is applied via vapor deposition, such as via atomic layer deposition for example. Application of a coating material via atomic layer deposition permits non-line-of-sight coating because a molecular layer of various germicidal chemical compounds may be formed anywhere the vapor makes contact.

By mounting one or more light sources 52 capable of emitting a germicidal ultraviolet light along the flow path of the cabin recirculation air, the light sources 52 may be used to continuously disinfect the airflow and/or a portion of a duct 24, without exposing aircraft occupants to any harmful effects from exposure to a high intensity ultra-violet light. Further, the sterilization system could continuously operate when the vehicle is both airborne and grounded without the need for any chemical means of rendering airborne viruses and bacteria harmless. Additionally, the one or more ultraviolet light sources 52 are small, use minimal power, and do not require high power, heat, or chemicals to kill viruses and bacteria.

The term "about" is intended to include the degree of error associated with measurement of the particular quantity based upon the equipment available at the time of filing the application.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. An air management system of a vehicle having a conditioned area comprising:
   at least one duct defining a flow path for delivering air to the conditioned area; and
   a sterilization system associated with the at least one duct, the sterilization system including at least one light source operable to emit a germicidal ultraviolet light into the flow path defined by the at least one duct to sterilize the air to be provided to the conditioned area;
   wherein the air output from the conditioned area is dehumidified upstream from the sterilization system and is rehumidified downstream of the sterilization system.

2. The air management system of claim 1, wherein the germicidal ultraviolet light has a wavelength between about 200 nm and about 280 nm.

3. The air management system of claim 1, wherein air within the at least one duct has a first flow rate at a first portion of the at least one duct and a second flow rate at a second portion of the at least one duct, the second flow rate being slower than the first flow rate, the at least one light source being positioned to emit the germicidal ultraviolet light within the second portion of the at least one duct.

4. The air management system of claim 3, further comprising a filter mounted within the second portion of the at least one duct, the at least one light source being positioned to emit the germicidal ultraviolet light over a portion of the filter.

5. The air management system of claim 1, further comprising a filter mounted within the at least one duct, wherein the at least one light source is positioned to emit germicidal ultraviolet light over a portion of the filter.

6. The air management system of claim 1, wherein a surface of the at least one duct associated with the at least one light source is reflective.

7. The air management system of claim 1, wherein the at least one light source operable to emit a germicidal ultraviolet light into the flow path defined by the at least one duct includes a first light source and a second light source, spaced from the first light source, wherein the germicidal ultraviolet light emitted by the first light source overlaps with the germicidal ultraviolet light emitted by the second light source.

8. The air management system of claim 7, wherein the first light source and the second light source are mounted in vertical alignment.

9. The air management system of claim 7, wherein the first light source and the second light source are mounted adjacent opposite sides of the at least one duct.

10. The air management system of claim 7, wherein the first light source and the second light source are mounted at adjacent sides of the at least one duct.

11. The air management system of claim 1, further comprising:
    an air source;
    an environmental control system in fluid communication with the air source;
    a cabin air recirculation system fluidly connected to an outlet of the conditioned area;
    an air mixing unit connected to the environmental control system and to the cabin recirculation air system; and
    an air distribution system extending from the air mixing unit to one or more vents associated with the conditioned area.

12. The air management system of claim 11, wherein the at least one duct is a part of the cabin recirculation air system.

13. The air management system of claim 11, wherein the at least one duct is the air mixing unit.

14. The air management system of claim 11, wherein the at least one duct is a part of the air distribution system.

15. The air management system of claim 1, wherein the conditioned area is a cabin of an aircraft.

16. The air management system of claim 15, wherein the air is cabin recirculation air provided from an outlet of the conditioned area.

17. The air management system of claim 15, wherein the sterilization system is operational when the aircraft is in flight.

18. The air management system of claim 1, wherein the at least one light source includes a plurality of light sources, wherein the plurality of light sources and an intensity of each of the plurality of light sources is determined based on at least one of a volume flow rate and a humidity of the air.

19. The air management system of claim 1, wherein the air is dehumidified upstream from the sterilization system.

20. The air management system of claim 19, wherein the air is rehumidified downstream of the sterilization system.

* * * * *